US006955665B2

(12) United States Patent
Domeier et al.

(10) Patent No.: US 6,955,665 B2
(45) Date of Patent: Oct. 18, 2005

(54) TAMPON WRAPPER WITH IMPROVED OPENING MEANS

(75) Inventors: Wolfgang Werner Hans Domeier, Kreuzau-Drove (DE); Charles John Berg, Jr., Wyoming, OH (US); James Henry Barton, Oberems (DE); Francis Michael Nicholas, Addlestone (GB); Ricky Alan Pollard, Moscow, OH (US); William Francis Search, Jr., Middletown, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 245 days.

(21) Appl. No.: 10/154,305

(22) Filed: May 23, 2002

(65) Prior Publication Data
US 2003/0220624 A1 Nov. 27, 2003

(51) Int. Cl.[7] .................. A61F 13/20; B65D 85/08; B65D 75/00
(52) U.S. Cl. .................. 604/385.02; 206/440; 206/824
(58) Field of Search .................. 604/904, 385.02, 604/385.17, 385.18, 363; 206/210, 363, 440, 206/824

(56) References Cited

U.S. PATENT DOCUMENTS

| 2,285,542 A | * | 6/1942 | Tasker ..................... 229/87.05 |
| 3,358,686 A | * | 12/1967 | Asaka .......................... 604/14 |
| 3,856,143 A | * | 12/1974 | Simon et al. ............... 206/438 |
| 4,170,305 A | | 10/1979 | Hull, Jr. et al. |
| 4,610,659 A | | 9/1986 | Friese |
| 4,676,773 A | * | 6/1987 | Sheldon ....................... 604/16 |
| 5,050,742 A | | 9/1991 | Muckenfuhs |
| 5,133,457 A | * | 7/1992 | Kadel .......................... 206/438 |
| 5,134,832 A | | 8/1992 | Pesendorfer et al. |
| 5,471,820 A | | 12/1995 | Oppe et al. |
| 5,765,682 A | * | 6/1998 | Bley et al. ................. 206/363 |
| 6,036,679 A | * | 3/2000 | Balzar et al. ............... 604/387 |
| 6,183,457 B1 | | 2/2001 | Kuhn |
| 6,293,932 B1 | * | 9/2001 | Balzar et al. ............ 604/385.02 |
| 6,478,763 B1 | * | 11/2002 | Simonsen et al. ............. 602/79 |
| 2003/0220625 A1 | * | 11/2003 | Domeier et al. ........ 604/385.12 |

FOREIGN PATENT DOCUMENTS

| DE | 29620118 U1 | | 4/1998 |
| DE | 102 14 579 A1 | * | 10/2003 ........... B65D 75/58 |
| EP | 0213241 | | 3/1987 |
| EP | 0 418 791 B1 | | 3/1994 |
| EP | 0 509 666 B1 | | 5/1996 |
| EP | 0 711 705 A2 | | 5/1996 |
| EP | 0 597 446 B1 | | 4/1998 |
| EP | 1 010 622 A1 | | 6/2000 |
| GB | 2 227 666 A | | 8/1990 |
| WO | WO 96/23711 A1 | | 8/1996 |
| WO | WO 00/59437 A1 | | 10/2000 |
| WO | WO 01/36272 A1 | | 5/2001 |

* cited by examiner

Primary Examiner—Larry I. Schwartz
Assistant Examiner—Michael G. Bogart
(74) Attorney, Agent, or Firm—Ingrid N. Hickman; Kevin C. Johnson

(57) ABSTRACT

The present invention relates to a wrapper for individually packaging absorbent articles for personal hygiene, especially tampons. The wrapper of the present invention is provided with an opening means, which prevents the wrapper from becoming separated into more than one piece of wrapper material upon being opened.

21 Claims, 7 Drawing Sheets

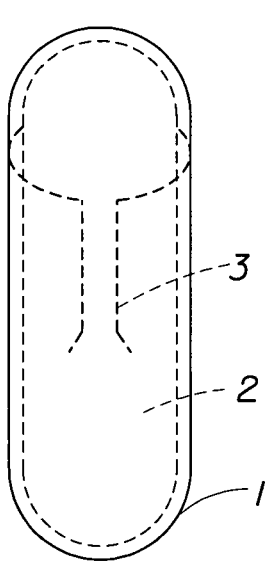
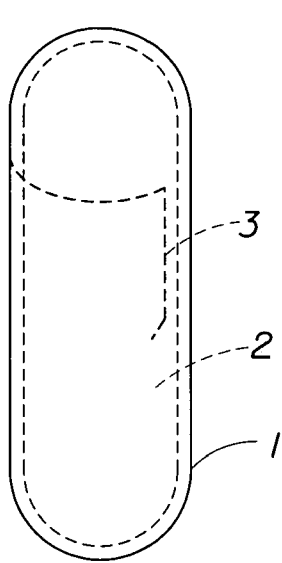
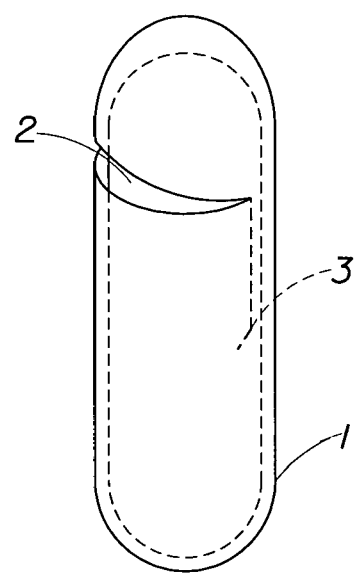
Fig. 1a  Fig. 1b  Fig. 1c
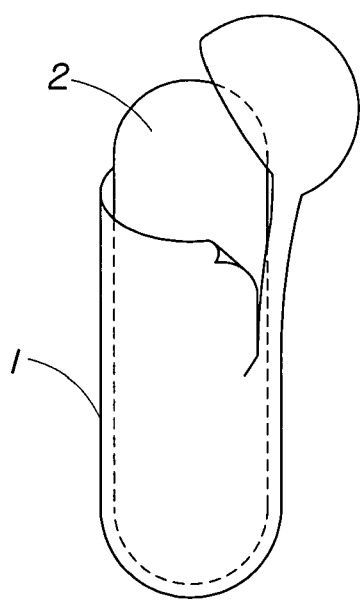
Fig. 1d
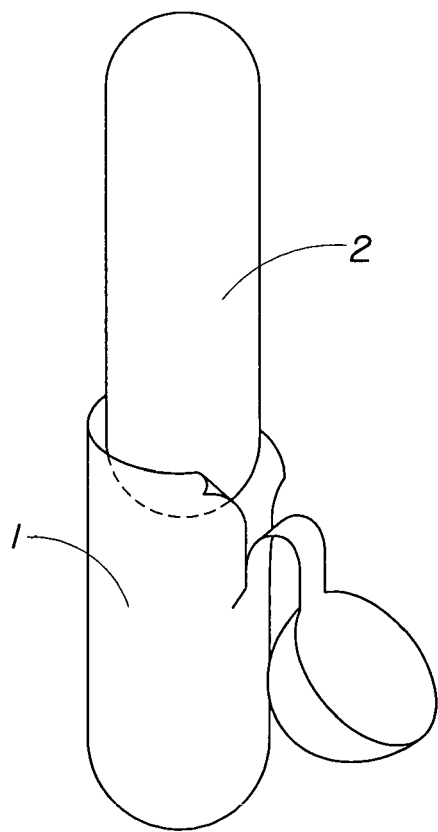
Fig. 1e

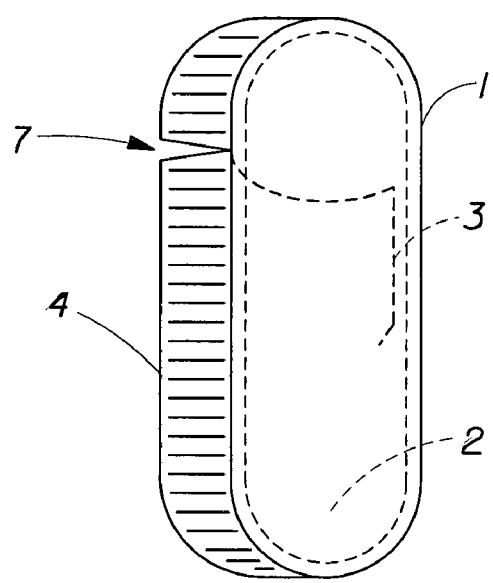
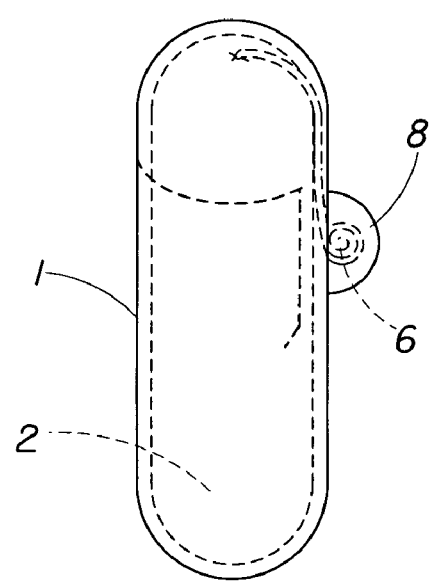
Fig. 4      Fig. 5
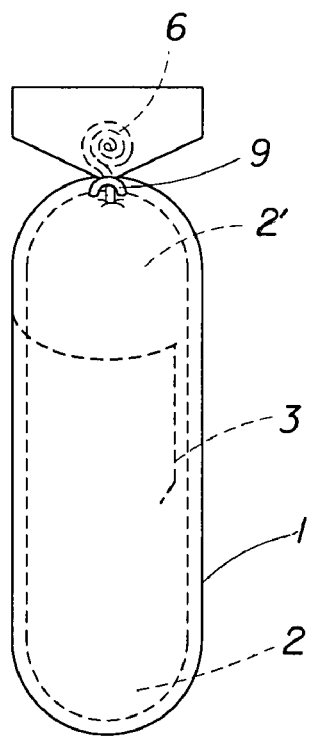
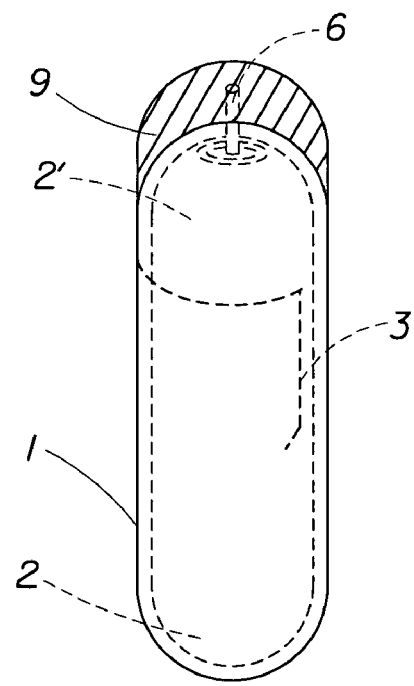
Fig. 6a      Fig. 6b

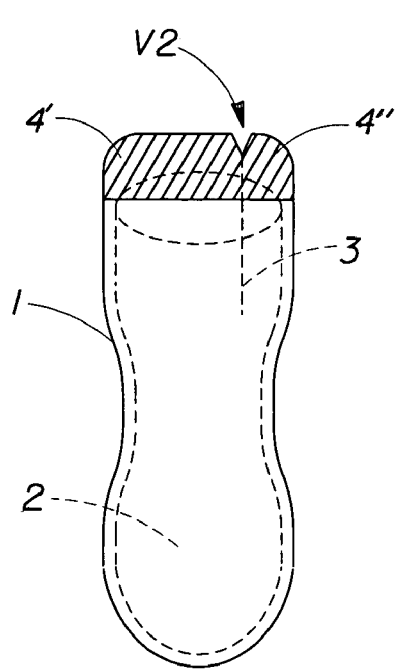
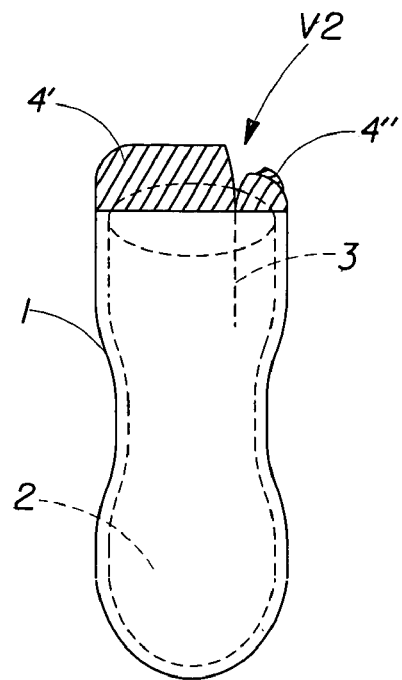
Fig. 8a  Fig. 8b
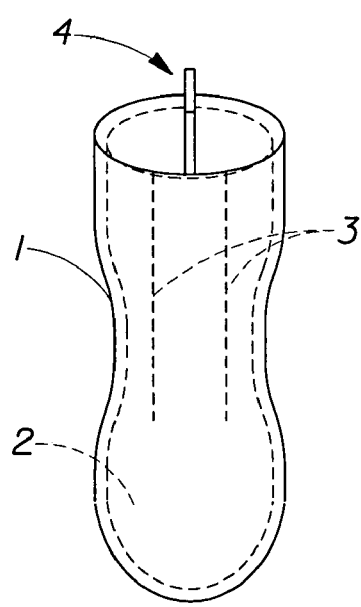
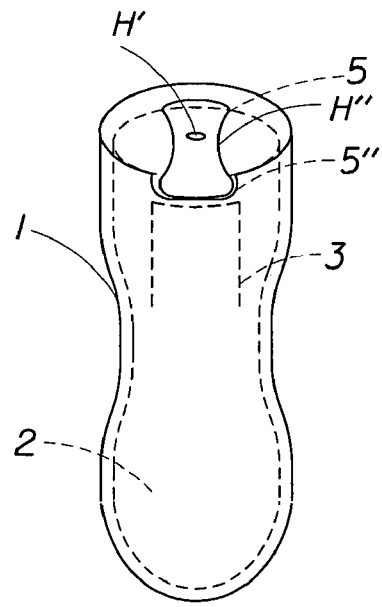
Fig. 8c  Fig. 9a

TAMPON WRAPPER WITH IMPROVED OPENING MEANS

FIELD OF INVENTION

The present invention relates to a wrapper for individually packaging absorbent articles for personal hygiene, especially tampons. The wrapper of the present invention is provided with an opening means, which prevents the wrapper from becoming separated into more than one piece of wrapper material upon being opened.

BACKGROUND OF THE INVENTION

Absorbent articles for personal hygiene, especially those for feminine protection, are typically individually packaged for hygiene reasons. The packaging prevents the articles from being soiled, e.g. by dust, unintended touching and the like. Tampons are typically packaged individually into wrappers for guaranteeing hygienic conditions. These wrappers fully enclose the tampon and consist in most cases of plastic film, such as films made of polyethylene, polypropylene or cellophane. The usual way of opening such wrappers in order to release the tampon for topical application is to separate the wrapper into multiple pieces, whereby creating an opening in the wrapper, through which the tampon can be released. An example for such an opening mechanism is disclosed on EP-A-597,446. This document teaches an airtight tampon wrapper having a line of weakness extending around the whole circumference of the wrapped tampon. By acting on the wrapper on both sides of the line of weakness the wrapper is opened, whereby being separated into at least two non-connected parts. Other commercially available possibilities for opening tampon wrappers include separating the wrapper into multiple pieces by e.g. using tear tapes (e.g. Tampax® or Always® digital tampons).

All current methods for opening tampon wrappers have one drawback in common: They are generating several pieces of waste originating from the wrapper. These pieces have to be collected and disposed. Furthermore, it is inconvenient for the user of the tampon to handle several pieces of waste material originating from the tampon wrapper during the process of inserting a tampon. Thus, it would be beneficial to have a tampon wrapper substantially enclosing an individual tampon in a hygienically satisfying manner, which wrapper is still constituted of a single piece of material even after being opened for releasing the tampon. Accordingly, it is an object of the present invention to provide an improved tampon wrapper fulfilling the above requirements by being provided with an opening means preventing the wrapper from becoming separated into more than one piece of wrapper material upon opening of said wrapper.

SUMMARY OF THE INVENTION

The tampon wrapper of the present invention, which is intended for being used for individually packaging of absorbent articles, in particular tampons, is provided with an opening means comprising at least one line of weakness and being able to prevent the wrapper from becoming separated into more than one piece of wrapper material upon opening.

BRIEF DESCRIPTION OF THE DRAWINGS

FIGS. 1a–e show an exemplary embodiment of the wrapper 1 of the present invention and the mechanism for opening of this wrapper 1. In FIGS. 1a and 1b an exemplary line of weakness 3 according to the present invention is illustrated.

FIG. 3b illustrates the mechanism of opening of the wrapper of the embodiment shown in FIG. 3a.

FIG. 4 illustrates a wrapper 1 according to the present invention designed to adjust the initial tear force required for opening of the wrapper 1.

FIG. 5 illustrates a wrapper 1 according to the present invention having a cord deployment means 8 for containing the removal cord 6 of the tampon 2 in a more spaced-away relationship from the tampon 2 in order to aid the removal cord 6 to be grasped more easily.

FIGS. 6a and b illustrate a wrapper according to the present invention having alternative cord deployment means featuring a compressed zone 9, said cord deployment means pulling a portion of the removal cord 6 away from the tampon 2 upon opening of the wrapper 1 for aiding the removal cord 6 to be grasped more easily.

FIG. 7b is rotated 90 degrees in reference to FIG. 7a.

FIGS. 8a, 8b and 8c illustrate another preferred version of the wrapper 1 according to the present invention. FIG. 8c is rotated 90 degrees in reference to FIG. 8a. FIG. 8b illustrates the wrapper 1 partially torn open. In FIGS. 8a and b the rear vertical perforation is not shown.

FIGS. 9a–e illustrate additional executions for cord deployment means according to the present invention.

DETAILED DESCRIPTION OF THE INVENTION

Figures 2A, 2B:
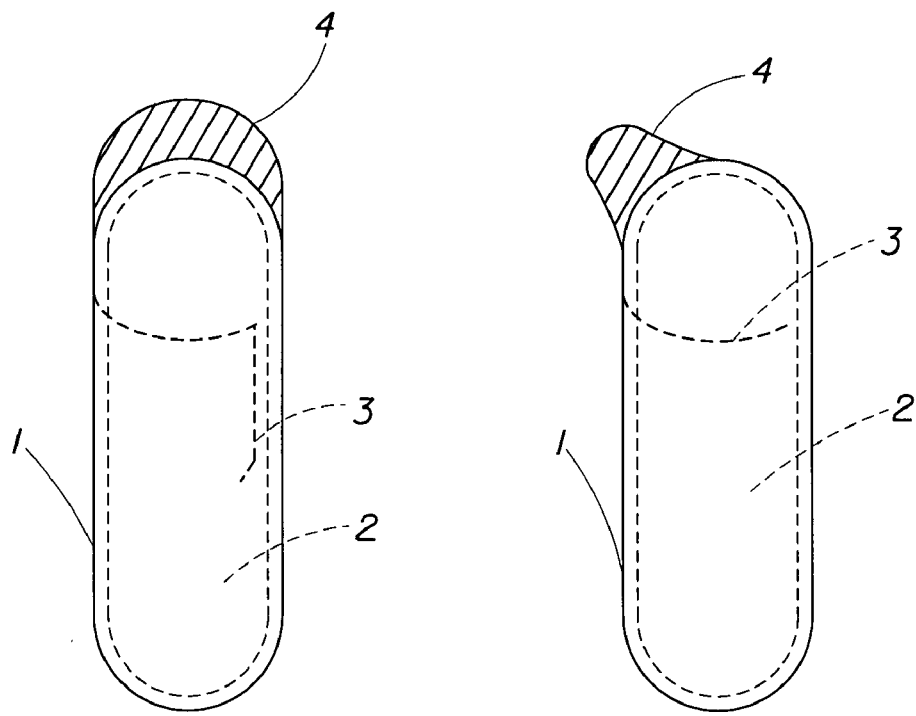
FIGS. 2a–c illustrate exemplary lines of weakness 3 as well as examples for opening aids 4, 4' and 4" according to the present invention.

The present invention refers to a wrapper for individually packaging absorbent articles, in particular tampons for feminine hygiene.

By 'tampon' it is meant herein an absorbent article, in some embodiments, a disposable one, comprising absorbent material usually being compressed into a self-sustaining, generally oblong, typically essentially cylindrical shape. In most cases the absorbent material comprises fibrous material, e.g. wood pulp fluff, cotton or the like. Tampons according to the present invention have an insertion end, a withdrawal end and a centre portion, said insertion end being opposed to said withdrawal end and said centre portion being located between said insertion end and said withdrawal end. In some embodiments, the insertion end is tapered and the withdrawal end is flared. In some embodiments, the tampon according to the present invention is also provided with a removal cord for allowing convenient removal of the used tampon from the region of use. The removal cord has two ends and is conventionally attached with one of said ends to the withdrawal end of the tampon, whereas the other end is referred herein as the free end. The removal cord can optionally be provided with a so-called secondary absorbent, which is a piece of absorbent material typically being located on the end of the removal cord being attached to the withdrawal end of the tampon. Secondary absorbents are used for absorbing fluid, which has leaked through or along the tampon and preventing this fluid from soiling the user's undergarments by flowing/being wicked along the removal cord. Tampons as used herein are suitable for various regions of use. The primary region of use is the female vagina, where the tampon is typically used for absorbing body fluids, especially menses. Typically, when being exposed to body fluids, the tampon will start to expand and thereby more or less lose its compressed self-sustaining shape. Another area of use involves other body cavities, where absorption of body fluids and/or application of medicine is intended, e.g. in the course of medical surgery. Tampon use is not only contemplated for human use, but can also be employed, particularly in administering medication, to other mammals.

The term 'use', as used herein, refers to the period of time that starts when the absorbent article is actually put in contact with the anatomy of the user.

By 'outer surface' of the tampon it is meant herein the visible surface of the compressed tampon prior to use or expansion.

By 'length' of a tampon it is meant herein the linear extension of a tampon along its largest dimension.

By 'perimeter' of a tampon it is meant herein the distance measured along the outer surface of the tampon in a portion of said outer surface extending in a plane being substantially perpendicular to the dimension of the length of said tampon. In other words, the length of the tampon extends along the x-axis of an orthogonal Cartesian coordinate system and the perimeter typically lies in the y,z-plane of said coordinate system. The perimeter of the tampon typically changes as a function of the length of said tampon.

'Wrapper' as used herein refers to a structure, which is formed of a wrapper material and which substantially encloses an individual absorbent article, in some embodiments, an individual tampon, for packaging purposes. The wrapper of the present invention is constituted of one connected piece of wrapper material, though a wrapper can also be made from multiple pieces of material sufficiently joined together such that it substantially acts as one connected piece of wrapper material. The wrapper has two ends, each of them being assigned to an end of the wrapped tampon. The wrapper of the present invention has an opening means that allows opening of the wrapper for releasing the wrapped tampon. The opening means comprises at least one line of weakness, which does neither extend around the whole wrapped tampon in terms of length nor perimeter. Because of this the wrapper is prevented from becoming separated into several pieces of wrapper material upon opening of the wrapper, which is facilitated by tearing along the line of weakness. The line of weakness of the present invention is however long enough to be able to create an opening in said wrapper, which is sufficiently large to allow release of the tampon therethrough.

By 'wrapper material' it is meant herein any material suitable to be used for hygienically wrapping tampons. Said wrapper material has two surfaces; the 'inner surface' is directed towards the wrapped tampon, whereas the 'outer surface' is aligned opposite to said inner surface. Typically, suitable wrapper materials for use herein are flexible polymeric films, having a thickness of less than 1 mm. Examples for wrapper materials suitable for use with the present invention are polymeric films made of polyethylene, polypropylene, polyester, cellophane, polyamide, poly(vinyl chloride), ethylene-vinyl acetate copolymer and the like. Alternatively, heat-shrinkable films, stretch films or pre-stretched elastic material can be used to form the wrapper of the present invention. While not limited to a given composition, preferred compositions of heat-shrinkable and stretch films comprise primarily polyolefins such as polyethylene and polypropylene, or polyvinyl chloride. Polystyrene and polyethylene-terephtalate (PET), although being not heat sealable, are also suitable for use with the present invention. Wrappers consisting of those materials can be closed by gluing with an adhesive. Other generally occlusive materials include metallic foils, such as aluminium foil. While occlusive wrapper materials are often preferred, in other situations non-occlusive or porous materials can be used, such as nonwovens, wovens, scrims, meshes and papers. Such non-occlusive materials can be made occlusive by combinations such as by lamination with or by coating with occlusive material. In the case of cellulosic papers, examples include lamination with a polymeric film such as a polyolefinic composition or coating or impregnation of the paper with wax. The aforementioned materials can be coated with various chemical compounds to improve their barrier properties or the ability for sealing. Any suitable combination of the aforementioned materials is also within the scope of the present invention. In some embodiments, the materials suitable for use as wrapper materials with the present invention are heat-sealable for forming the wrapper by closing the wrapper material via heat-sealing onto itself after having wrapped the tampon. Thereby a seam is generated in the regions of the wrapper, which were exposed to heat. Alternatives for closing the wrapper material are gluing, embossing, crimping, sewing, stitching, entangling, mechanical interlocking, cold pressure welding, or ultrasonic bonding. In some embodiments, the wrapper materials for use herein have a low flexural modulus for providing a low noise tampon wrapper during transport as well as during handling, i.e. opening of the wrapper.

It is preferred according to the present invention that the wrapper material tightly conforms to the outer surface of the wrapped tampon. This can be particularly well achieved by using heat-shrinkable or stretchable materials as wrapper material. 'Tightly conforming' of the wrapper to the outer surface of the wrapped tampon as used herein means that there is substantially no visually noticeable void space between the wrapper and the tampon. In other words, the perimeter of the tightly conforming wrapper on average exceeds the perimeter of the outer surface of the tampon by about 50%, about 30%, about 10% or even about 5%. Since the perimeter of a tampon can typically change as a function of the length of said tampon, especially because the tampon has often an insertion end with a tip or has tails or indents in its outer surface, the aforementioned limits for the tight conformation of the wrapper apply to at least all substantially lengthwise portions of the outer surface of the tampon, and in some embodiments, to all portions of the outer surface of the tampon. In some embodiments, of the present invention some regions of the wrapper material may provide additional functional benefits, such as cord deployment means. In these regions the wrapper material may not tightly conform to the outer surface of the tampon according to the definition herein. However, according to the present invention the wrapper material tightly conforms to the lengthwise portions of the outer surface of the tampon by at least about 70%, about 80% or even at least about 90% to the lengthwise portions of the outer surface of the tampon. As an example, the aforementioned perimeters of the wrapper and the tampon can be measured along the length of the tampon in steps of every 10% of the length of the tampon. Tightly conforming wrappers can be of particular use when so-called shaped tampons are wrapped, i.e. tampons having tails, indents or the like on their outer surface. Since tampons are typically made by compressing fibrous absorbent material into a self-sustaining shape, the tightly conforming wrapper can optionally be used to act with a certain compressing force on the outer surface of the tampon, which will aid maintaining said self-sustaining shape, in particular in the tailed or indented regions of the outer surface of the tampon, by counteracting the expansion of the compressed material.

'Heat-shrinkable' as used herein refers to materials, which have an extension in at least two dimensions, e.g. films or nonwovens, and which reduce their extension in at least one of said dimensions when being heated to an elevated temperature above normal storage or usage temperatures, but being lower than their melting temperature or being lower than their decomposition temperature in case the material decomposes prior to melting.

The wrapper of the present invention is provided with an opening means comprising at least one line of weakness, in some embodiments, one single line of weakness, said opening means being further able to prevent separation of the wrapper into more than one piece of wrapper material upon opening of the wrapper. Indeed, the line of weakness does neither extend around the whole length nor around the whole perimeter of the wrapped tampon in order to prevent tearing-off of parts of the wrapper upon opening of the wrapper, which would result in fragmentation of the wrapper. The line of weakness of the present invention is however long enough to be able to create an opening in said wrapper, which is sufficiently large to allow release of the tampon therethrough. By 'line of weakness' as used herein it is meant a number of weakness points being arranged in a row. This row does not necessarily have to be straight. Bent lines of weakness and lines of weakness changing direction by e.g. having angles or curves are expressly within the scope of the present invention. Lines of weakness can comprise segments that extend around the perimeter and along the length of the wrapper. When the line of weakness comprises a partial or complete perimeter direction, it is preferred that the perimeter segment of the line of weakness be located closer to the withdrawal end of the tampon versus the insertion end such that upon opening a portion of the withdrawal end of the tampon is exposed for release of the tampon. In those cases, the line of weakness according to the present invention extends around a part of the perimeter of the wrapped tampon, generally around at least about 5%, about 40%, or even about 60% of the perimeter of the wrapped tampon, while in any case extending around less than 100% of the perimeter. However, the line of weakness can extend around even up to 98% of the perimeter of the wrapped tampon.

When the line of weakness comprises a partial or complete length direction, it is preferred that a portion of the length segment of the line of weakness be located closer to the withdrawal end of the tampon versus the insertion end such that upon opening, a portion of the withdrawal end of the tampon is exposed as well as a portion of the length of the tampon is exposed for release of the tampon. In those cases, the line of weakness according to the present invention extends along a part of the length of the wrapped tampon, generally at least along about 5%, about 25%, and about 50% of the length of the wrapped tampon, while in any case extending around less than 100% of the length of the tampon. However, the line of weakness can extend around even up to about 98% of the length of the wrapped tampon, such that e.g. one starting point of the line of weakness is located close to the insertion end of the tampon, the line of weakness extends from there towards the withdrawal end and further extends, after having extended around the withdrawal end, again towards the insertion end of the tampon in a region of the wrapper, which is substantially opposite to the region where the line of weakness extends starting from said first end. The second end of the line of weakness is again close to the insertion end of the tampon.

Figure 2C:
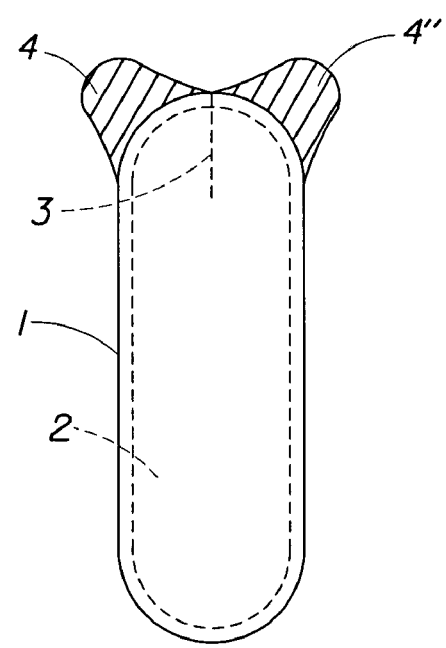

In a preferred embodiment the line of weakness according to the present invention extends around a part of the perimeter of the tampon and along a part of the length of the tampon. FIGS. 1a–e illustrate one example for the wrapper having a line of weakness according to the present invention and the opening procedure therefore. FIG. 1a shows the wrapper with the wrapped tampon, FIG. 1b shows the same wrapper and tampon, after a rotation of 90°. Opening of the wrapper 1 for releasing the tampon 2 along the line of weakness 3 results in an initial tearing step, during which the wrapper 1 mainly tears around the perimeter of the tampon 2 (FIG. 1c) and a subsequent step, during which the wrapper 1 tears mainly along the length of the tampon 2 (FIG. 1d). In FIG. 1e the tearing process is completed and the tampon 2 is released from the wrapper 1. It is generally preferred according to the present invention that the distance between adjacent weakness points is substantially equal throughout the line of weakness; however if desired, varied spacing can be employed to affect the tearing force profile (increase/decrease of tearing force upon tear propagation) experienced by the user as she initially tears and continues to open the wrapper along the line of weakness. A particularly preferred embodiment of the line of weakness of the present invention is a line of weakness extending around a part of the perimeter of the wrapped tampon, in some embodiments, 60%, or about 75% of the perimeter of the wrapped tampon; however, the line of weakness can even extend even more than 90% up to 98% of the perimeter of the wrapped tampon, and turns to extend along a portion of the length of the tampon. The result is a more or less symmetric line of weakness around the perimeter of the wrapped tampon as illustrated in FIGS. 1a and 1b. It is to be seen in FIGS. 1a and 1b that the line of weakness, after having extended around a part of the perimeter of the wrapped tampon, is then extending with both ends substantially parallel along the length of the wrapped tampon, thereafter the two ends are diverging for a short distance from each other in order to prevent accidental tear-off of the wrapper into multiple pieces at the end of the line of weakness. Alternatively, other configurations of the line of weakness, such as lines of weakness extending only around the perimeter of the wrapped tampon, such as illustrated in FIG. 2b, or lines of weakness extending only along the length of the wrapped tampon as illustrated in FIG. 2c are suitable for use herein.

Figure 7A:
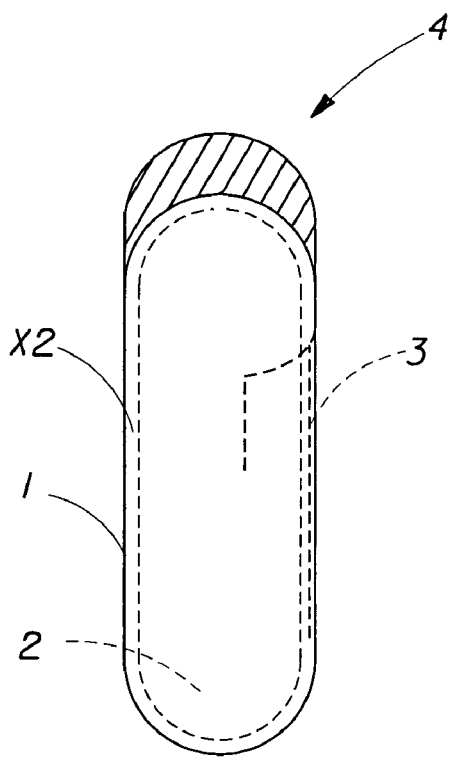
FIGS. 7a and 7b illustrate a wrapper 1 according to the present invention designed with a line of weakness pattern 3 that allows for the opening of the wrapper 1 when pulling opening aid 4 either forward or rearward. The opening aid 4 also illustrates a triangular shape.
Figure 7B:
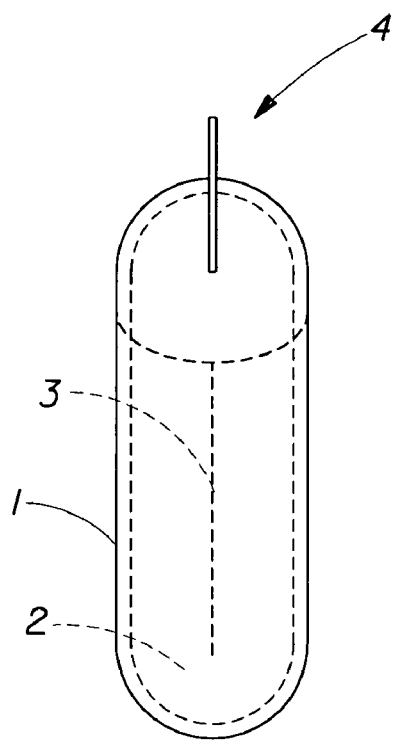
Figure 7C:
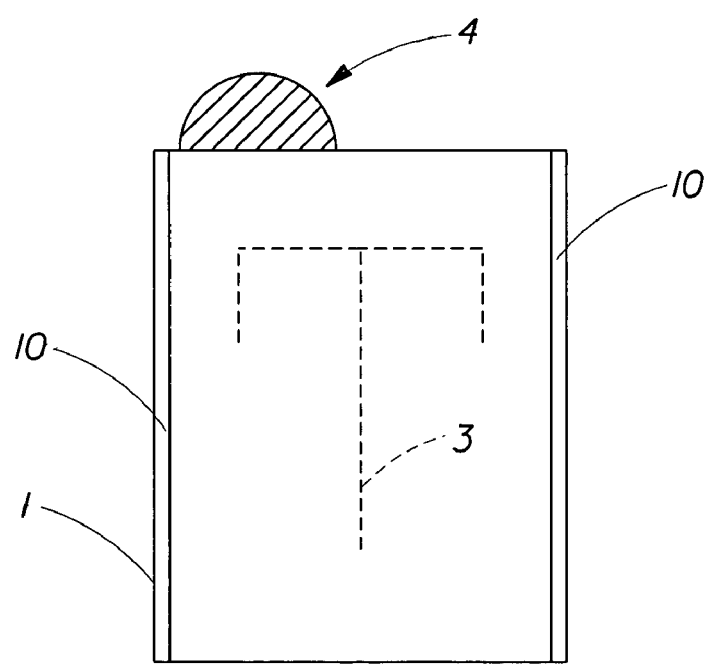
FIG. 7c shows the wrapper 1 of FIGS. 7a and b laid flat prior to wrapping, overlap sealing along the edge areas 10, and shrinking to the tampon 2.

In an alternate embodiment shown in FIGS. 7a–c, a line of weakness pattern 3 is in the shape of a "T" with a horizontal segment extending around a portion of the perimeter of the tampon and three vertical segments extending down along a portion of the length of the tampon. The centre segment extends further down along the length of the tampon than the two side segments, thereby the line of weakness loosely corresponding to a "T" shape when the wrapper is flattened into two dimensions such as shown in FIG. 7c. Looking at FIG. 7b, which is a 90 degree rotation of FIG. 7a, the flap 4 can be grasped and pulled either toward the front or the rear of the tampon and, in either direction, the wrapper will open by tearing along a portion of the line of weakness 3. This embodiment of the line of weakness permits multi-directional wrapper opening. Because of this particular line of weakness 3, it is not necessary that all segments need to separate or tear to afford convenient wrapper opening and tampon removal.

By 'weakness points' it is meant herein a region in the wrapper material where the thickness of the wrapper material is substantially less than the thickness of the wrapper material surrounding said region. The weakness points according to the present invention are in some embodiments, formed by depressions or perforations.

By 'depression' it is meant herein a weakness point, where inside of the region of the wrapper material forming the weakness point said wrapper material still has a thickness greater than zero. The depressions can extend into the wrapper material from the inner and/or from the outer surface of the wrapper material. Another preferred execution of the line of weakness according to the present invention is that the individual depressions are overlapping each other, so that a substantially continuous line of weakness formed by depressions is generated, in which the thickness of the wrapper material is substantially constant, such as a score line or groove.

By 'perforation' it is meant herein a weakness point, where in at least part of the region of the wrapper material forming the weakness point said wrapper material has a thickness of zero.

While a single line of weakness or a contiguous pattern of several portions of lines of weakness are often preferred, in certain cases it may be desirable to have two or more separate lines of weakness or two or more patterns. For example when two separate lines of weakness are used, their position on the wrapper relative to each other may be such that they are located in surface regions of the wrapper material that are relatively spaced-away from each other, or they can be located partially or wholly in close proximity to each other. An example of the latter is a wrapper with two straight lines of weakness that parallel each within the immediate vicinity or juxtaposed next to each other.

Optionally, the tampon wrapper of the present invention can comprise one or more opening aids. 'Opening aid' as used herein means any kinds of means for making it easier for the user to open the wrapper for releasing the tampon. This includes flaps extending from the outer surface of the wrapper material, in some embodiments, flaps comprising a portion of wrapper material protruding from the wrapper. 'Flap' as used herein means a portion of material extending from the outer surface of the wrapper and being sufficiently large to be reliably grasped by the user, thus providing for example a tab, handle or grip function. Optionally, such a protruding portion can be stiffened for better gripability by e.g. by embossing with or without the addition of heat. Other opening aids for being used with the present invention are pieces of material being attached to the wrapper material and protruding from the outer surface of the wrapper material, such as by adding a coating, or adding an additional layer of material, which can be another material or the wrapper material itself. A good example of integrally stiffening the protruding portion is by folding the material of said protruding portion over upon itself and then heat-seal it together. Examples of tampon wrappers of the present invention having opening aids are shown in FIGS. 2a–c. For opening of the wrapper shown in FIGS. 2 and b, the user holds the wrapped tampon 2 with one hand on one side of the line of weakness 3, whereas two or three fingers of the other hand acts on the protruding flap 4, being located on the other side of the line of weakness, to initiate opening of the wrapper 1. Another embodiment is shown in FIG. 2c, where two flaps 4' and 4" are arranged on both sides of a line of weakness 3, which extends more or less along the length of the wrapped tampon 2. By pulling both flaps 4' and 4" away from each other the wrapper 1 can be opened. A preferred embodiment of FIG. 2c is illustrated in FIGS. 8a–c where flaps 4' and 4" are partially spaced apart with an intervening tear initiation feature, in this case V-shaped cut V2. There are two lines of weakness that partially extend along the length of the tampon into and over the withdrawal end of the tampon whereupon they join together and extend up the flap 4' and 4" boundary area where they terminate at the V-shaped cut V2 space. Referring to FIG. 8a, the front-facing line of weakness 3 is shown while the opposing rear-facing line of weakness is hidden behind tampon 2. FIG. 8c shows the same wrapper and tampon of FIG. 8a, after a rotation of 90° around the length of the tampon. In FIG. 8c, the combined flap 4' and 4" is shown edge-on and centred between the front and rear and both lines of weakness 3 can be seen extending along the front and rear faces of the wrapper where they meet (not shown) near the intersection of the flap 4 with the portion of wrapper 7 covering the withdrawal end of the tampon 2. FIG. 8b has the same orientation as FIG. 8a but illustrates the wrapper 7 partially torn open. In FIGS. 8a and 8b, the V-shaped cut V2 is not centred from side to side such that the width and area of flap 4' is larger than the width and area of flap 4". This allows the user to use treat and grasp flap 4' as an anchor while grasping flap 4" and tearing down the side. This results in a main portion of the wrapper contiguous with flap 4' to still enclose more than 50% of the perimeter tampon 2 to avoid inadvertent and premature fallout of the tampon 2 from the wrapper while the user is still grasping and pulling flap 4" during wrapper opening.

The flap opening aid as described above, while often being stiffer than the wrapper material itself, often is still somewhat flexible. However, more rigid or thicker opening aids made from a material different than the wrapper can be quite useful. Plastic sheeting, molded plastic parts, extruded plastic parts, cardboard, cellulosic board are examples of materials that are generally stiffer as well has thicker than many wrapper materials. Foams sheets can be suitably used which are thicker than the wrapper and can optionally be more rigid than the wrapper. While less preferred, stiffer materials that are thinner than the wrapper can be employed such as cast glass, ceramics, specialized polymers, and metallic compositions such as in screening. In the case of more rigid materials, the increased rigidity of such opening aids allow them to transmit the user-applied opening force along or through at least a portion of the more rigid opening aid where in certain configurations, possibly in combination with the product and wrapper, it mechanically leverages the user's force in opening the package.

The more rigid opening aids can be in any form, including but not limited to: rings, caps, plates, curved plates, sticks, discs, asymmetrical structures, meshes, screens, flared structures, molded parts, cut or stamped sheets, etc. One way to determine whether one structure, such as an opening aid, is more rigid than the wrapper material is to conduct a comparison via a simple drape test using a flat horizontal surface which intersects a vertical surface to produce a straight edge. In the case of comparing two films or flat sheets, equivalent-sized samples of equal width and length are prepared. Then each sample is fully laid on the flat horizontal surface with one end in the lengthwise direction positioned just above the straight edge such that the width dimension of the sample is parallel to the straight edge. Both samples are then advanced a portion of the length of the samples to an appropriate distance beyond the vertical edge such that an equivalent length of material of the samples overhang beyond the vertical surface. The overhanging material will be unsupported against the force of gravity and may therefore bend or drape toward the ground. The remainder material still supported on the horizontal surface may be optionally anchored in static position by use of an anchoring force such as a weight, clamp, etc. Next, the greatest vertical distance of the unsupported overhanging edge of the samples from the horizontal surface is measured (i.e. essentially this provides a relative elevation difference). The sample that demonstrates the smaller vertical distance from the horizontal surface is considered to be more rigid. In the case where both materials are not readily converted into flat samples, other known techniques can be used to compare the rigidity of opening aid and wrapper material, in at least one appropriate direction or dimension, versus the wrapper material. For example, in the case of many typical non-flat molded or laminated materials, they often are more rigid than typical films employed for wrapping—and various techniques could demonstrate this, even a modified drape test where the typical molded or laminated material may only drape or bend a nearly imperceptible amount under reasonable test conditions while the wrapper sample would noticeably drape or bend.

The opening aids can be of varying thickness and can have thick or feathered edges. The opening aid can be of any color or graphic appearance. The opening aids can have drape-enhancing or drape-suppressing elements built into them such as score lines, hinge points, ribbing, filament reinforcements, etc. such that the opening aid is either drape-enhanced or drape-suppressed in at least one of the directions of interest within the opening aid. The opening aids can be produced from any material or composition, including but not limited to: single or multiple ply materials, polymer resins, polyolefins, papers, cardboard, aluminum, steel, biodegradable resins such as BAK 1095 (available from Bayer), Eastar Bio (available from Eastman Chemicals) for example a blown 37 micron Eastar Bio film, Mater-Bi (available from Novamont), Biomax (available from DuPont), Bionelle (available from Showa High Polymer), Lunare SE (available from Nippon Shokubai), Eco-PLA (available from Dow Cargill), Exoflex (available from BASF), Biotec (available from Kashoggi), and Vinex (available from Air Products) and starch-filled materials, water-soluble resins and the like. Typically, one opening aid is used, however the wrapper of the present invention can possess multiple opening aids.

In some embodiments, a portion of the opening aid extends or protrudes beyond the circumscribed volume of the tampon in such a manner that the user can easily contact and grasp the opening aid to directly apply force to the wrapper portion with the intent for opening. The opening aid is engaged (e.g. adhered, banded, bonded, conformed around protruding or into indented aid features, etc) to at least a portion of the wrapper such that after the wrapper is sufficiently opened to permit removal of the tampon (or withdrawal of the wrapper from the tampon) it still is engaged with at least a portion of the wrapper for more convenient discarding of the package materials by the consumer, i.e. one piece. The opening aid can be positioned on the external surface of the wrapper; however, the more rigid opening aid or major portion thereof is in some embodiments, located inside the wrapper.

Figure 3A:
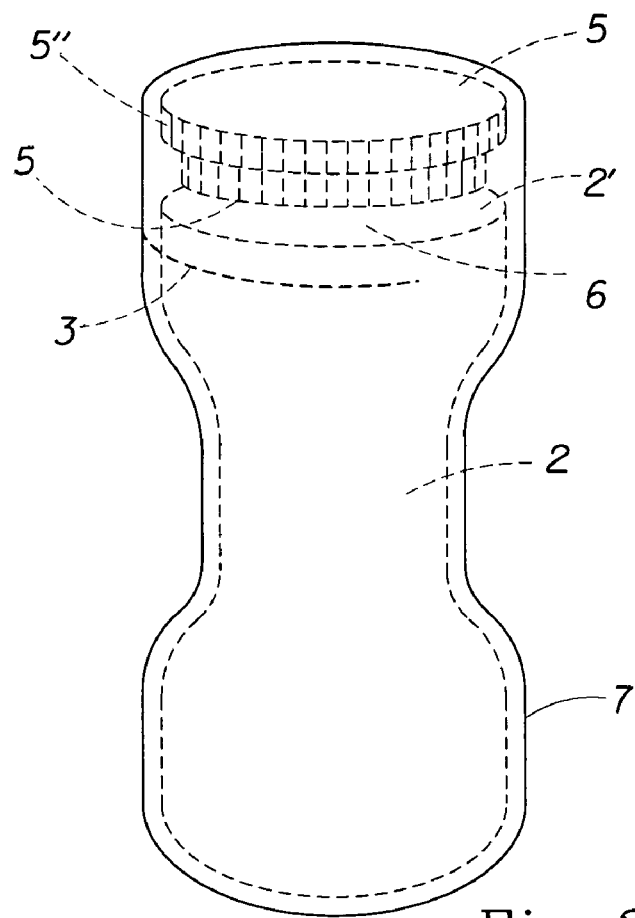
FIG. 3a illustrates a specific embodiment of the wrapper of the present invention being provided with a cap 5 of rigid material for aiding the opening of the wrapper 1.
Figure 3B:
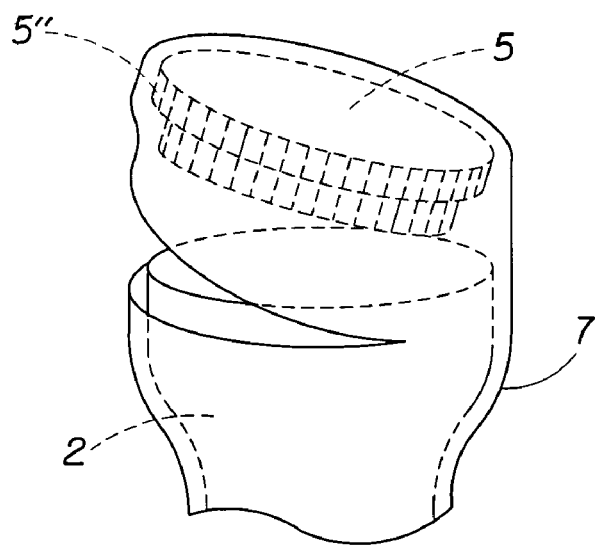

A particularly preferred embodiment of the more rigid opening aid according to the present invention is a cap. 'Cap' as used herein means a rigid structure typically having for example a substantially cylindrical or substantially semi-spherical shape. The cap of the present invention is wrapped together with the tampon by the wrapper of the present invention and has a cavity with at least one opening on at least one side, in some embodiments, on a flat side of said cap, said opening being located directly adjacent to one end, in some embodiments, the withdrawal end, of the tampon, so that no wrapper material is situated between the cap and the tampon. FIG. 3 illustrates this specific embodiment. The user can, by acting on the cap 5 through the wrapper material, easily open the wrapper 1, because the force applied to a portion of the lip 5" of the rigid cap 5 will aid tearing the line of weakness 3. Another specific benefit associated to this embodiment is the possibility of providing a containment area for the removal cord 6 of the shaped tampon 2. The removal cord 6 is situated inside of the cap 5 bordering with its open side 5' to the withdrawal end 2' of the shaped tampon 2. This allows the removal cord 6 to be maintained in a more spaced-away relation to the shaped tampon 2 and thus in a less compressed condition. By this, the removal cord 6 can be grasped by the user much more easily once the wrapper is opened, thus making the use of a shaped tampon 2, or any tampon, wrapped according to this specific embodiment much more convenient. In FIG. 3b the preferred mechanism of opening of the embodiment of the wrapper of the present invention shown in FIG. 3a is illustrated. In some embodiments, the user holds the wrapped tampon in one hand by putting her forefinger around the perimeter of the tampon 2, so that the end of the tampon 2 having the cap 5 adjacent thereto is directed towards the thumb of the same hand. Then by pushing a portion of the lip 5" of the cap 5 away from the tampon 2 with the aforementioned thumb, while said thumb is located approximately in the middle of but opposite to the two ends of the line of weakness 3, the wrapper 1 can be opened along the line of weakness 3. The arrow in FIG. 3b illustrates the preferred location of the thumb and its movement. In this example, the wrapper permits easy one-handed opening by the user. The cap is engaged to a portion of the wrapper such that to prevent separation of the cap from wrapper into more than one piece of packaging material upon opening of the wrapper. One preferred technique for actively engaging the cap with the wrapper is to utilize a heat-shrinkable wrapper material such that the heat-shrunk material applies a compression tension about at least an element or portion of the cap to engage it, such as in this case the underside of the lip 5". While a lip or other protrusion element of cap 5 is preferred, a cap without such a feature can also provide aid in opening the wrapper 7.

Opening aids like flaps as described above can fulfil further functions: These flaps can be used for controlling the tear force required for opening of the wrapper along the line of weakness. One possible embodiment is illustrated in FIG. 4. The flap 4 formed by an extension of the wrapper material is situated along the length of the wrapped tampon 2 and has a cut 7, which corresponds to the line of weakness 3 of the wrapper 1. Due to the cut 7 the force required for tear initiation in order to open the wrapper 1 is significantly reduced. Another embodiment could be designed for achieving the opposite in order to avoid unintended opening during transport. This can be facilitated by providing the wrapper with a flap like the one in FIG. 4 except the fact that the flap is not cut, but an extension of the line of weakness comes to the edge of the flap 4. Due to the higher thickness of the material to be torn for opening the wrapper (the flap in this example is formed by two layers of wrapper material) the force required for tear initiation, which means tearing of the flap along the extended line of weakness, is significantly higher than the force required for tear propagation.

Furthermore, the initial tear force could be adjusted via adjusting the position of the cut in combination with the weakness line in relation to one of the ends of the tampon. In the embodiment illustrated in FIG. 4 a part of the wrapper needs to be pulled over the withdrawal end of the tampon. The closer the cut and the weakness line is located to the tampon withdrawal end, the less material needs to be pulled over the withdrawal end of the tampon and the lower is the initial tear force for opening the wrapper. On the other end, the more the cut and the weakness line are shifted towards the direction of the insertion end of the tampon, the more material must be pulled over the withdrawal end of the tampon and the higher is the initial tear force.

'Cord deployment means' as used herein refers to constructions for locating at least a portion of the removal cord of the tampon. In some embodiments, cord deployment means are also spacing away at least a portion of the removal cord from the surface of the tampon. By this, the user can better grasp the removal cord in preparation for applying the tampon compared to conventionally wrapped tampons, where the removal cord is always very tightly pressed onto the outer surface of the tampon and therefore being difficult to grasp. An example of the cord deployment means according to the present invention is illustrated in FIG. 5, where a portion of the wrapper 1, which does not tightly conform to the outer surface of the tampon 2, forms a pocket 8 for containment of the removal cord 6. Alternative cord deployment means are shown in FIGS. 6a and b. In FIGS. 6a and b, a portion of the wrapper extends beyond the withdrawal end 2' of the tampon 2. At least a part of the wrapper material extending beyond the withdrawal end 2' is compressed in a compressed zone 9. The removal cord 6 extends through the compressed zone 9, thereby getting attached to a certain degree to the wrapper 1 in said compressed zone 9. By opening of the wrapper 1 through tearing of the line of weakness 3 the compressed zone 9 is withdrawn from the tampon 2 and thereby also the removal cord 6 is pulled away from the tampon 2, which aids the removal cord 6 to be grasped by the user. The compressed zone 9 can be made by application of pressure and optionally heat to at least a part of the portion of the wrapper material extending beyond the end of the tampon 2. In EP-A-965,316 a method of heat sealing of the free end of the removal cord to the bottom of the tampon wrapper is disclosed, which also leads to loosening the free end of the removal cord from the tampon for better gripability. In this context it is preferred by the present invention that the attachment of the portion of the removal cord, which is extending through the compressed zone to said compressed zone is primarily achieved by frictional forces. Alternatively, if an opening aid is employed, it can also be constructed such that it retains in later-releasable fashion a portion of the cord to cause spacing away of at least a portion of the removal cord from the surface of the tampon. An example is the embodiment of the wrapper of the present invention being provided with a cap, which is illustrated in FIGS. 3a and b and is described hereinbefore.

An alternate way to releasably capture a portion of the cord is to thread it through a loop or aperture or compressively capture it in a tight fitting notch whereas the loop or aperture or tight fitting notch, which compressively squeezes the cord radially, is associated with one of the portions of the wrapper being pulled away from the tampon body such that it partially pulls away a portion of the cord in a spaced away configuration relative to the tampon. The captured portion of the cord can be automatically released when the tampon wrapper is nearly or fully opened, thereby exposing some free cord that is easy for the user to grasp; or, the user can grasp the portion of the cord that spans the two wrapper elements and release it herself from the loop, aperture or notch. The loop, aperture or notch can be part of the wrapper itself, part of an opening aid or a separate element associated with either the wrapper or an opening aid. As a separate element it can be engaged, adhered or fastened to the wrapper (e.g. interior or exterior surface) or an opening aid and can comprise, by example, a small piece of film, paper or board with an aperture or notch in it or configured into a loop such as by using a strap or filament of material.

Figure 9B:
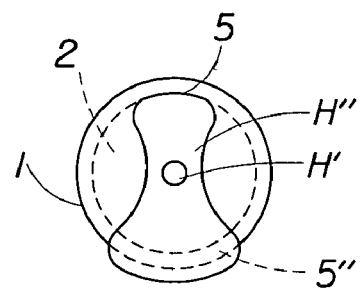
Figure 9C:
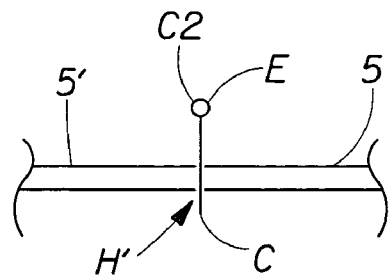
Figure 9D:
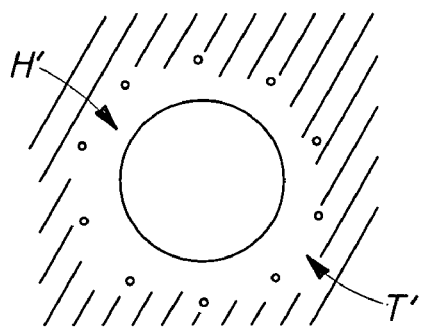
Figure 9E:
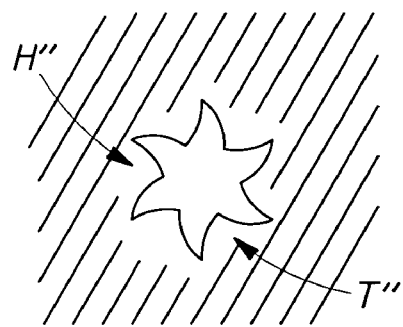

Alternatively, as illustrated in FIGS. 9a–e, the aperture or notch can be a portion of an opening aid, e.g. a more rigid shaped top plate 5 that rests atop the withdrawal end of the tampon 2. The plate 5 is wrapped in between the wrapper 7 and the tampon 2 and has an extending lip 5" for user ease in applying a force to the line of weakness 3 in FIG. 9a. The top view FIG. 9b shows both an aperture H' and a notch H" for releasably capturing a portion of the cord. In FIG. 9c a cross-section of the plate 5 is shown with cord C passing through aperture H'; the wrapper and tampon are not shown. Depending upon the degree of dimensional interference or contact clearance between the aperture H' and the cord C, when the plate 5 is separated or lifted from the withdrawal end of the tampon 2, it will either pull some of the cord below plate 5 up and away from the withdrawal end of the tampon; or, it will travel along the cord C located above plate 5 toward cord end E such that some of the cord C will pass through the aperture H' from above the plate 5 to below the plate 5. Optionally, there can be a knot or other increased perimeter element C2 of the cord located above the plate 5. The increased perimeter element C2 can act as a temporary catch to interfere with aperture H' to cause the wrapper opening motion transmitted through plate 5 to pull some of the cord C below the plate 5 away from the withdrawal end of the tampon 2. The interference between the increased perimeter element C2 should be such that under increased force, which is still reasonable for the user to exert, the increased perimeter element C2 either compresses, undoes itself or elongates to pass through the aperture; or, the material around the aperture deforms to allow the passage of the increased perimeter element C2. In a top view of the region near the aperture FIG. 9d, the material around the aperture T' could have a low resistance to flexing due to gauge, form or material composition. Alternatively, in a top view of the region near the aperture FIG. 9e the perimeter of the aperture can be formed such that inward projecting tabs or teeth will flex open under reasonable force to allow C2 to pass through.

Generally, the wrapper of the present invention in its most generic form can be made by wrapping wrapper material around the tampon and sealing it onto itself for closing the wrapper material in order to substantially enclose the tampon. The sealing is in some embodiments, facilitated by pressure and optionally heat. In another embodiment of the invention a sleeve of the wrapper material is formed and connected with an adhesive in an overlapping region. The sleeve can be put over the tampon and then heat shrunk. If needed, the end of the wrapper being assigned to the withdrawal and/or the insertion end of the tampon could be closed with an adhesive in order to form a pouch that is heat shrunk in the next step.

In order to achieve tight conformation of the wrapper material to the tampon it is preferred to use shrinkable, especially heat-shrinkable, material, which is shrunk after being closed around the tampon, in order in decrease the dimensions of the wrapper material, so that the wrapper tightly conforms to the outer surface of the tampon. The same can be achieved by using stretch films, or even pre-stretched elastic material, which is allowed to relax into a non- or low-tensed or non- or low-stretched state after being closed around the tampon. Another alternative for achieving tight conformation of the wrapper to the outer surface of the tampon is partially closing the wrapper after having wrapped the wrapper material around the tampon, then evacuating the interior of the wrapper by application of vacuum and finally completely closing the wrapper.

Despite the fact that the present invention has been illustrated hereinbefore exclusively by examples for use as so-called digital tampons, i.e. tampons for use without applicator, the present invention is also applicable to applicator tampons.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. A wrapper (1) for an individual tampon (2) for feminine hygiene, said tampon (2) having an insertion end, a withdrawal end (2'), a centre portion, a perimeter, a length and an outer surface, said insertion end being opposed to said withdrawal end (2') and said centre portion being located between said insertion and said withdrawal end (2'), said wrapper (1) being constituted of one connected piece of wrapper material or several pieces of wrapper material, which are sufficiently bonded together to act as one connected piece, said wrapper having an inner surface directed towards said tampon (2) and an outer surface being aligned opposite to said inner surface, said wrapper (1) substantially enclosing said tampon (2), said wrapper (1) having two ends, one being assigned to said insertion end of said tampon (2) and one being assigned to said withdrawal end (2') of said tampon (2), said wrapper (1) having an opening means, said opening means allowing opening of said wrapper (1) for releasing said tampon (2), said opening means comprising at least one line of weakness (3), wherein said line of weakness (3) extends around less than the whole of said perimeter and the whole of said length of said tampon (2), said line of weakness preventing separation of said wrapper (1) into more than one piece of wrapper material upon opening.

2. Wrapper (1) according to claim 1, wherein said line of weakness (3) extends less than 98% of said perimeter and/or said length of said tampon (2).

3. Wrapper (1) according to claim 1, wherein said wrapper material tightly conforms to the outer surface of the wrapped tampon.

4. Wrapper (1) according to claim 1, wherein said line of weakness (3) is provided by weakness points being spaced from adjacent weakness points by essentially the same distance within said line of weakness (3).

5. Wrapper (1) according to claim 4, wherein said weakness points are constituted by depressions in said wrapper material, said depressions extending into said wrapper material.

6. Wrapper (1) according to claim 4, wherein said weakness points (3) are constituted by perforations in said wrapper material.

7. Wrapper (1) according to claim 1, wherein said tampon further comprises a removal cord, said removal cord comprising one end being attached to said withdrawal end of said tampon and one free end.

8. Wrapper (1) according to claim 1, wherein said line of weakness (3) is arranged around said tampon (2) partially around the perimeter of said tampon (2) and partially along the length of said tampon (2).

9. Wrapper (1) according to claim 1, wherein at least one end of said wrapper comprises an opening aid (4, 4', 4", 5).

10. Wrapper (1) according to claim 9, wherein said opening aid is a flap (4, 4', 4") extending from said outer surface of said wrapper material.

11. Wrapper (1) according to claim 10, wherein said flap (4) extends along the length of said tampon (2) and/or said withdrawal end (2') of said tampon (2) and is provided with a means being connected to said line of weakness (3), said means allows to adjust the force required for initiation of opening of said wrapper (1) along said line of weakness (3).

12. Wrapper (1) according to claim 11, wherein said means comprises an extension of said line of weakness (3) into said flap (4).

13. Wrapper (1) according to claim 9, wherein said opening aid is at least partially wrapped by said wrapper together with said tampon, such that at least a portion of said opening aid is located between said outer surface of said tampon and said inner surface of said wrapper material.

14. Wrapper (1) according to claims 13, said opening aid being constituted by a rigid cap, wherein said rigid cap (5) has a cavity with at least one opening (5') on at least one side, said opening (5') being directly adjacent to one end of said tampon (2).

15. Wrapper (1) according to claim 14, wherein said cap (5) is directly adjacent said withdrawal end (2') of said tampon (2).

16. Wrapper (1) according to claim 7, further comprising a cap (5), wherein at least a portion of said removal cord (6) is located in said cap (5).

17. Wrapper (1) according to claim 7, wherein said wrapper (1) further comprises a cord deployment means for locating at least a portion of said removal cord (6) spaced away from said tampon (2) for providing more ease of grasping of said removal cord (6) upon unpacking said tampon (2).

18. Wrapper (1) according to claim 17, wherein said cord deployment means is formed by said wrapper material in a region where said wrapper material forms a pocket (8) on said outer surface of said tampon (2).

19. Wrapper (1) according to claim 17, wherein said cord deployment means is formed by a part of said wrapper material extending beyond one end, said withdrawal end (2'), of said tampon (2), said part of said wrapper material being compressed in a compressed zone (9), a part of said removal cord (6) extending through said compressed zone (9) and being attached to said wrapper material in said compressed zone (9), so that said removal cord (6) is pulled away from said tampon (2) upon opening of said wrapper (1).

20. Wrapper (1) according to claim 17, wherein said cord deployment means is formed by threading said removal cord (6) through a loop or aperture (H', T', T") associated with said wrapper (1), or by compressively capturing said removal cord (6) in a tight fitting notch (H") associated with said wrapper (1).

21. A wrapper (1) for an individual tampon (2) for feminine hygiene, said tampon (2) having an insertion end, a withdrawal end (2'), a centre portion, a perimeter wherein said perimeter is a distance measured along an outer surface of the tampon in a portion of said outer surface extending in a plane being substantially perpendicular to the dimension of a length of said tampon, the length and the outer surface, said insertion end being opposed to said withdrawal end (2') and said centre portion being located between said insertion and said withdrawal end (2'), said wrapper (1) being constituted of one connected piece of wrapper material or several pieces of wrapper material, which are sufficiently bonded together to act as one connected piece, said wrapper having an inner surface directed towards said tampon (2) and an outer surface being aligned opposite to said inner surface, said wrapper (1) substantially enclosing said tampon (2), said wrapper (1) having two ends, one being assigned to said insertion end of said tampon (2) and one being assigned to said withdrawal end (2') of said tampon (2), said wrapper (1) having an opening means, said opening means allowing opening of said wrapper (1) for releasing said tampon (2), said opening means comprising at least one line of weakness (3), wherein said line of weakness (3) extends around less than the whole of said perimeter and the whole of said length of said tampon (2), said line of weakness preventing separation of said wrapper (1) into more than one piece of wrapper material upon opening.

\* \* \* \* \*